United States Patent [19]

Blair

[11] Patent Number: 5,295,996
[45] Date of Patent: Mar. 22, 1994

[54] PRESSURE WRAP DEVICE

[76] Inventor: Dean H. Blair, 7837 Metacomet Rd., Hanover, Md. 21076

[21] Appl. No.: 906,098

[22] Filed: Jun. 29, 1992

[51] Int. Cl.⁵ ............................................. A61B 17/12
[52] U.S. Cl. .................................... 606/203; 128/119.1
[58] Field of Search ...................... 606/204, 189, 203; 128/119.1

[56] References Cited

U.S. PATENT DOCUMENTS 4,308,861  1/1982  Kelly ..................................... 606/204
4,479,495  10/1984  Isaacson ............................... 606/204

FOREIGN PATENT DOCUMENTS 2566660  1/1986  France ................................. 606/189

Primary Examiner—Michael H. Thaler
Attorney, Agent, or Firm—Leon Gilden

[57] ABSTRACT

A tourniquet device is arranged for securement about a limb of an individual in cooperation with a major cardiovascular pressure point, wherein an elastomeric strap is securable at its ends having a semi-spherical projection mounted to a top surface of the strap for projection against the aforenoted pressure point. A modification of the invention includes adjustment structure for the projection to include an accessory projection, or alternatively an adjustable projection, mounted to the strap structure.

2 Claims, 5 Drawing Sheets

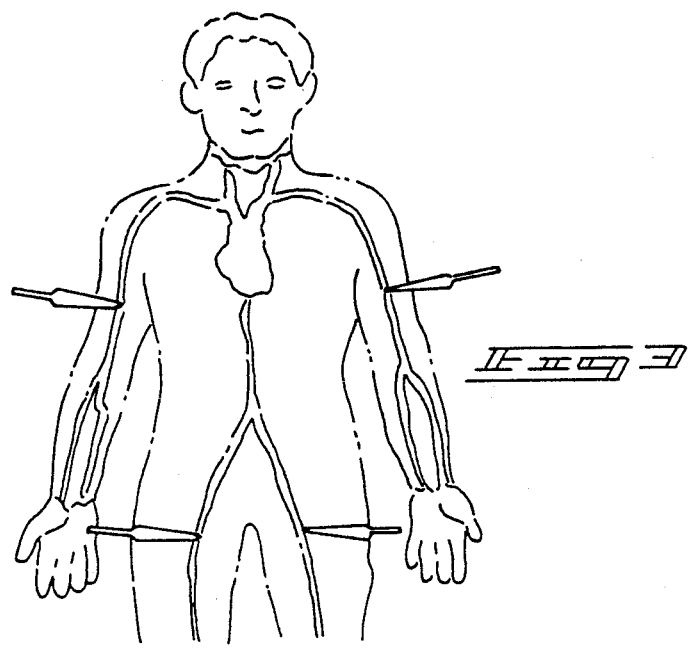
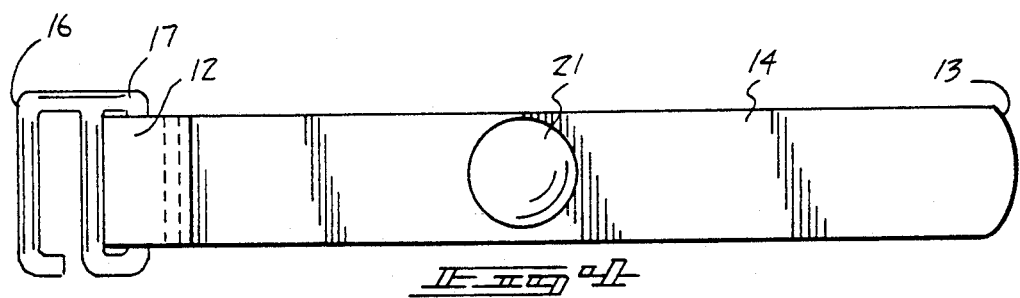
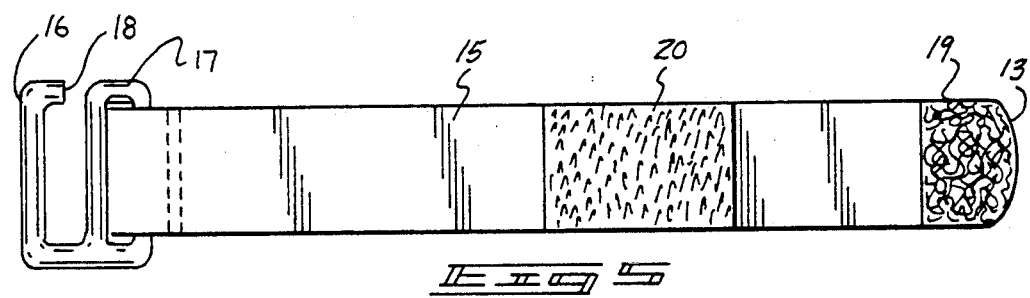

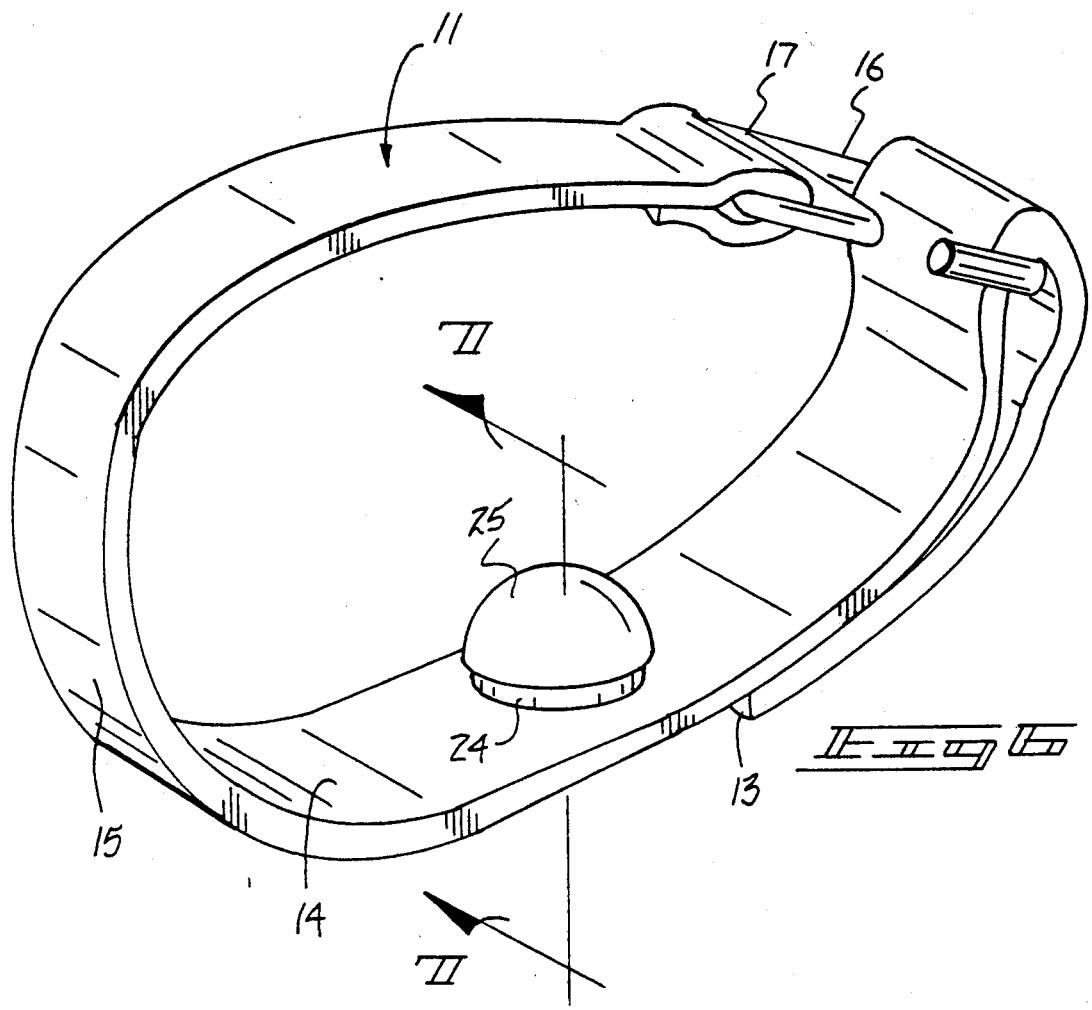
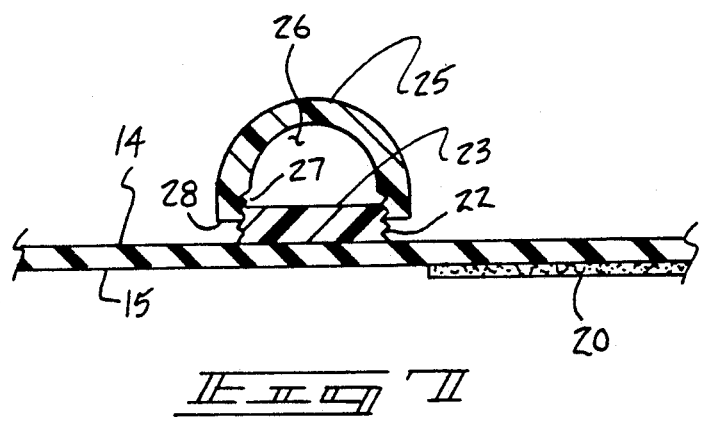

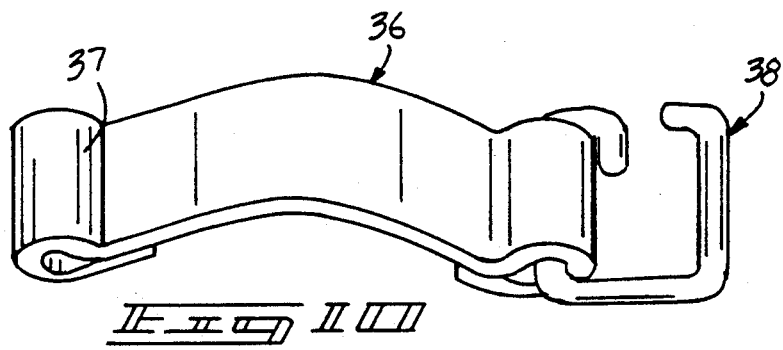
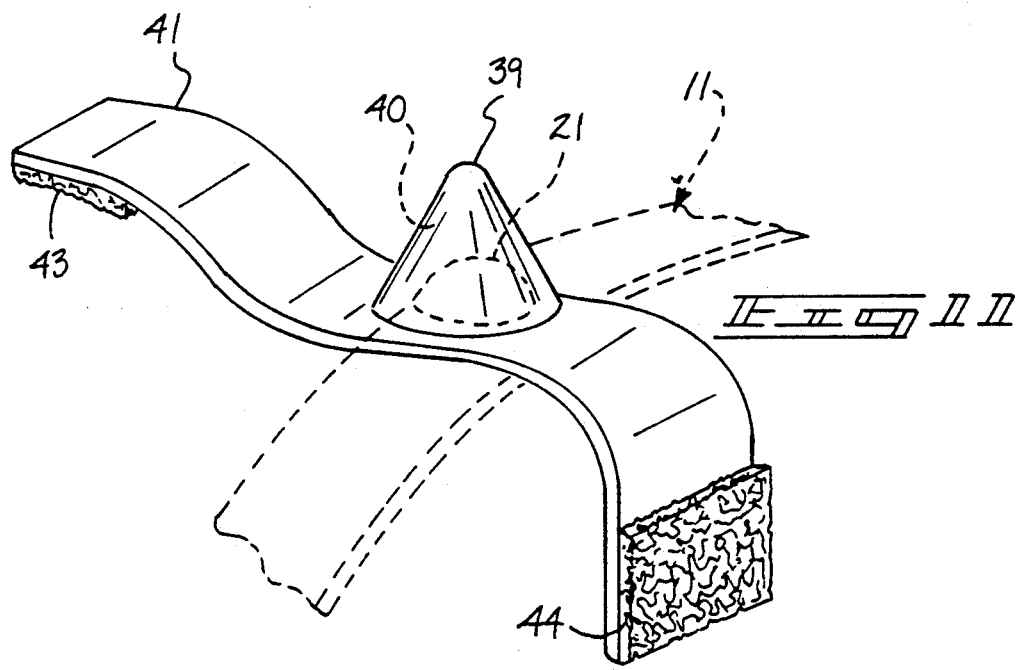
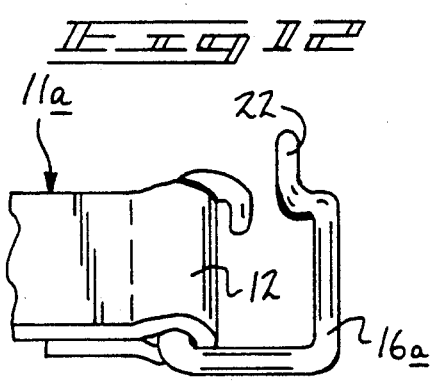
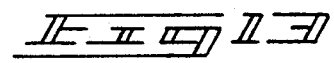

PRESSURE WRAP DEVICE

BACKGROUND OF THE INVENTION

1. Field of the Invention

The field of invention relates to tourniquet apparatus, and more particularly pertains to a new and improved pressure wrap device wherein the same is arranged for securement about an individual's limb to limit bleeding during and subsequent to injury.

2. Description of the Prior Art

Tourniquet devices of various types have been utilized throughout the prior art and exemplified in the U.S. Pat. Nos. 4,911,162; 4,640,821; 4,637,394; 4,297,996; and 3,628,536.

Heretofore, however, the prior art has failed to provide for a tourniquet structure accommodating ease of manipulation of the strap structure to position a projection relative to an individual to limit hemorrhaging subsequent to injury and in this respect, the present invention substantially fulfills this need.

SUMMARY OF THE INVENTION

In view of the foregoing disadvantages inherent in the known types of tourniquet apparatus now present in the prior art, the present invention provides a pressure wrap device wherein the same is directed to apply pressure to a cardiovascular pressure point to minimize hemorrhaging subsequent to injury. As such, the general purpose of the present invention, which will be described subsequently in greater detail, is to provide a new and improved pressure wrap device which has all the advantages of the prior art tourniquet apparatus and none of the disadvantages.

To attain this, the present invention provides a tourniquet device arranged for securement about a limb of an individual in cooperation with a major cardiovascular pressure point, wherein an elastomeric strap is securable at its ends having a semi-spherical projection mounted to a top surface of the strap for projection against the aforenoted pressure point. A modification of the invention includes adjustment structure for the projection to include an accessory projection, or alternatively an adjustable projection, mounted to the strap structure.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved pressure wrap device which has all the advantages of the prior art tourniquet apparatus and none of the disadvantages.

It is another object of the present invention to provide a new and improved pressure wrap device which may be easily and efficiently manufactured and marketed.

It is a further object of the present invention to provide a new and improved pressure wrap device which is of a durable and reliable construction.

An even further object of the present invention is to provide a new and improved pressure wrap device which is susceptible of a low cost of manufacture with regard to both materials and labor, and which accordingly is then susceptible of low prices of sale to the consuming public, thereby making such pressure wrap devices economically available to the buying public.

Still yet another object of the present invention is to provide a new and improved pressure wrap device which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic diagrammatic illustration of pressure points of an individual's cardiovascular system.

FIG. 4 is an orthographic top view of the strap structure.

FIG. 5 is an orthographic bottom view of the strap structure.

FIG. 6 is an isometric illustration of a modified strap structure utilizing an adjustable projection.

FIG. 7 is orthographic view, taken along the lines 7—7 of FIG. 6 in the direction indicated by the arrows.

FIG. 10 is an isometric illustration of an extension strap utilized by the invention.

FIG. 11 is an isometric illustration of an accessory projection utilized by the invention.

FIG. 12 is an isometric illustration of a further connector member utilized by the invention.

FIG. 13 is an orthographic end view of the connector member as illustrated in FIG. 12.

DESCRIPTION OF THE PREFERRED EMBODIMENT

Figure 1:
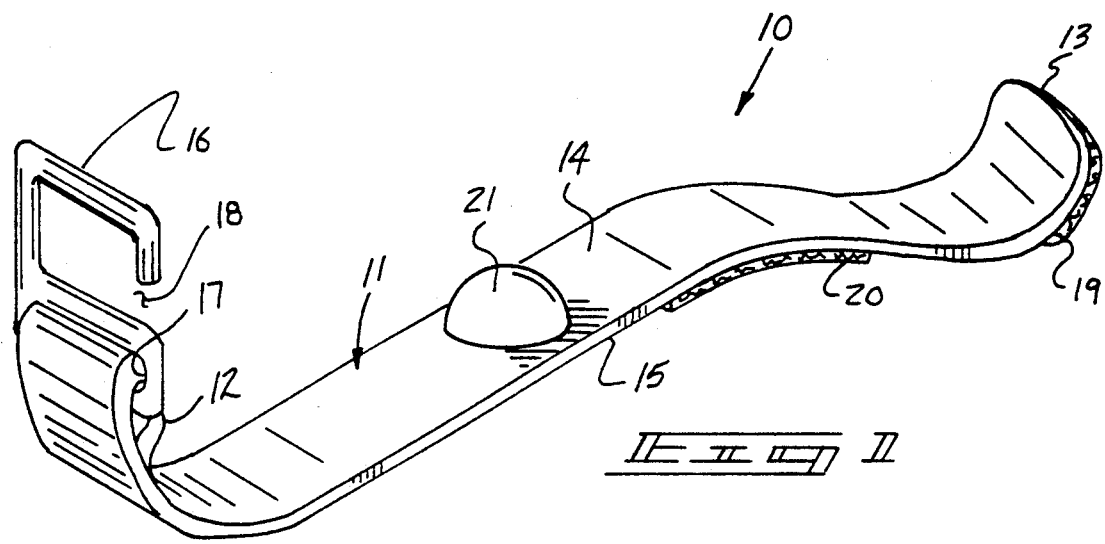
FIG. 1 is an isometric illustration of the instant invention.
Figure 2:
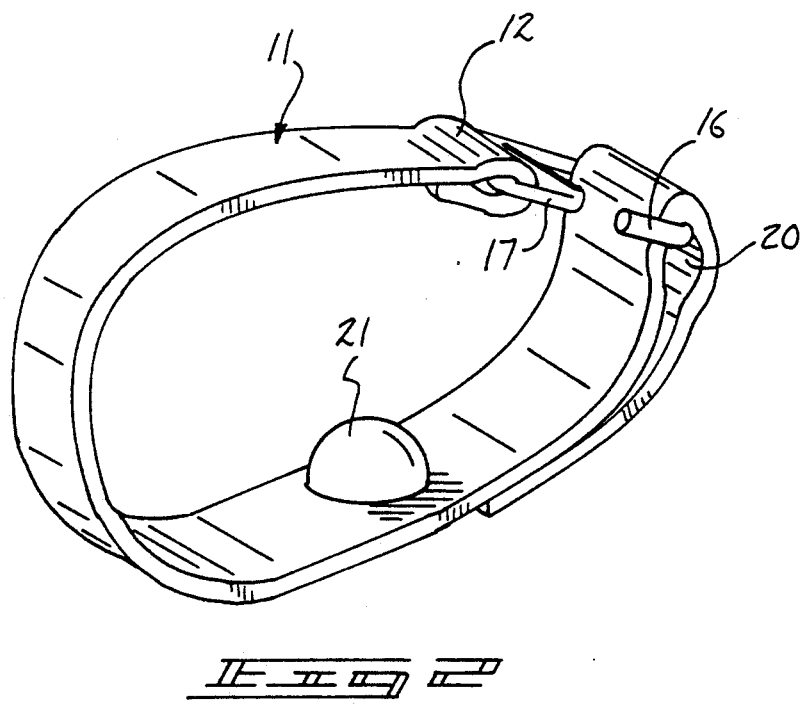
FIG. 2 is an isometric illustration of the invention in secured orientation relative to itself.

With reference now to the drawings, and in particular to FIGS. 1 to 13 thereof, a new and improved pressure wrap device embodying the principles and concepts of the present invention and generally designated by the reference numeral 10 will be described.

More specifically, the pressure wrap device 10 of the instant invention essentially comprises an elastomeric strap 11 having a strap first end loop 12 and a strap second end 13. A strap top surface 14 is spaced from a strap bottom surface 15. The strap first end loop 12 mounts a connector loop 17 of a connector member having a C-shaped connector leg 16 mounted to the loop defining a connector gap 18 to receive a second loop 22 formed when a first hook and loop fastener patch 19 mounted to the bottom surface 15 at the second end 13 connects with a second hook and loop fastener patch 20 spaced from the first hook and loop fastener patch 19 between the first hook and loop fastener patch 19 and a semi-spherical projection 21 fixedly mounted to and medially of the top surface 14. Application of projection 21 to one of the pressure points is indicated diagrammatically in FIG. 3 is available to limit excessive bleeding subsequent to an injury.

The FIGS. 6 and 7 indicate the semi-spherical projection structure formed with a cylindrical support hub 23 having an externally threaded cylindrical side wall 24 receiving a semi-spherical cap 25 thereon. The cap 25 includes a cap cavity 26 having an internally threaded wall surface 27 selectively securable about the externally threaded side wall 24, with the threads of the internally threaded wall 27 connecting the lower annular end 28 of the cap structure 25.

Figure 8:
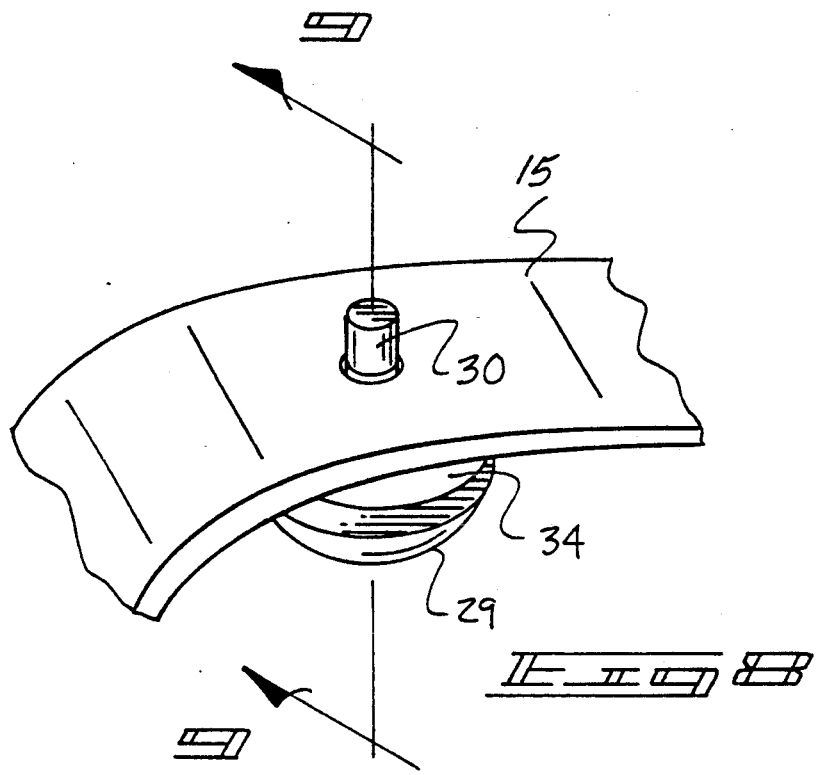
FIG. 8 is an isometric illustration of a further modified projection member utilized by the invention.
Figure 9:
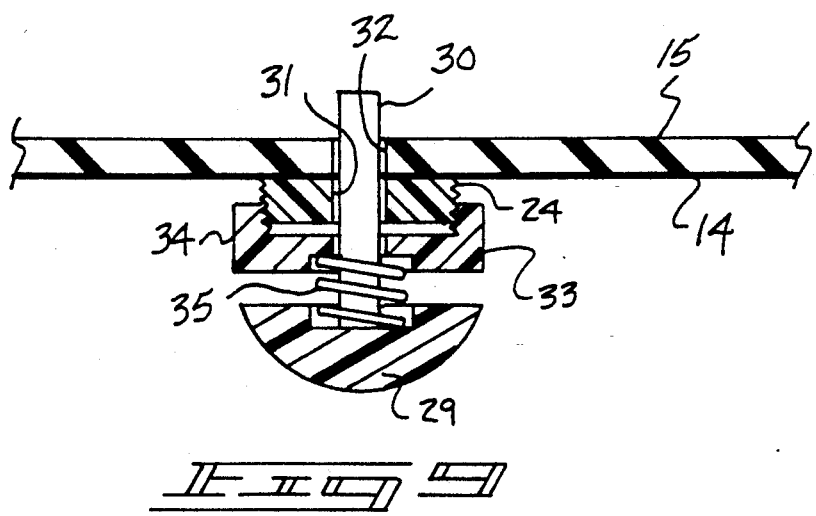
FIG. 9 is an orthographic view, taken along the lines 9—9 of FIG. 8 in the direction indicated by the arrows.

The FIGS. 8 and 9 indicates a further modified projection structure having a semi-spherical cap head 29 formed with an indicator rod 30 coaxially and integrally relative to the cap head 29. The indicator rod 30 is slidably received through a support hub bore 31 and a strap bore 32 that are coaxially aligned relative to the indicator rod 30 and the semi-spherical cap head 29. An intermediate cap 33 has a cap internally threaded lower skirt 34 adjustably securable along the externally threaded side wall 24 to effect adjustment of projection of the cap head 29 relative to a presatire point. A spring member 35 interposed between the cap head 29 and the intermediate cap 33 effects biasing pressure relative to the individual in use, wherein for a pulse indicator, the strap structure may be merely loosened, wherein pulsing of an associated artery and pressure point effects pulsing of the indicator rod 30.

The FIG. 10 indicates the use of a strap extension 36 having a strap extension first end loop 37 and a strap extension second end connector 38 permitting extension of the strap structure as required in various lengths typically from three through twelve inches. In this manner, use of the organization more readily about an individual's leg portions is availed.

An accessory projection 39 to provide for a greater pressurizing of a pressure point is provided having an accessory projection cavity 40 to receive the semi-spherical projection 21 or the cap head 29 or semi-spherical cap 25 as desired. The accessory projection 39 is mounted to an accessory flexible band 41 having an accessory band first end fastener 43 selectively securable to a flexible band second end fastener 44 about the existing strap 11, in a manner as indicated in FIG. 11.

The FIGS. 12 and 13 illustrate the use of a modified connector leg 16a having an extension tang 45 permitting ease of alignment and positioning of the modified connector leg relative to the second loop structure 22 of the strap structure 11.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A pressure wrap device, comprising,
    an elastomeric strap, the strap having a strap first end and strap second end, the strap first end having a first end loop, and
    the strap second end including a connector, the connector having a connector loop receiving the first end loop, and
    a C-shaped connector leg extending from the connector loop, with a connector gap oriented between the connector leg and the connector loop, and
    the strap having a strap bottom surface and a strap top surface, the strap top surface including a semi-spherical projection, and
    the strap bottom surface including a first hook and loop fastener patch adjacent the strap second end, and a second hook and loop fastener patch spaced from the first hook and loop fastener patch, and between the first hook and loop fastener patch and the projection, wherein the first hook and loop fastener patch is securable to the second hook and loop fastener patch to configure a second loop to receive the connector leg, and
    the projection includes a cylindrical support hub fixedly mounted medially of the elastomeric strap, the support hub including an externally threaded cylindrical side wall, and cap means adjustably mounted relative to the externally threaded side wall for effecting adjustable projection of the cap means relative to the strap top surface, and the cap means includes a cylindrical intermediate cap, the intermediate cap including an internally threaded lower skirt adjustably and threadedly securable to the externally threaded side wall of the support hub, and the intermediate cap having an intermediate cap bore, the support hub having a support hub bore, and the strap having a strap bore, wherein the strap bore, the hub bore, and the intermediate cap bore are coaxially aligned, and further including a semi-spherical cap head having a cap head planar bottom surface having an indicator rod fixedly and coaxially mounted to the cap head, wherein the indicator rod is slidably received through the intermediate cap bore, the support hub bore, and the strap bore, and a spring member interposed between the intermediate cap and the cap head wound about the indicator rod.

2. A pressure wrap device as set forth in claim 1 further including an accessory projection, with the accessory projection having a cavity arranged for receiving the cap head, the intermediate cap, and the support hub therewithin, the accessory projection mounted to a flexible band, with the flexible band including a flexible band opening in communication with the cavity, the flexible band having a flexible band first end fastener and a flexible band second end fastener to selectively secure the flexible band about the strap.

* * * * *